United States Patent
Christiansen et al.

[11] Patent Number: 6,058,157
[45] Date of Patent: May 2, 2000

[54] BONE DENSITOMETRY APPARATUS

[75] Inventors: Claus Christiansen, Vedbaek; Annette Møllgaard, Glostrup; Steen Værnholdt, Vig, all of Denmark

[73] Assignee: Osteometer MediTech A/S, Horsholm, Denmark

[21] Appl. No.: 09/188,333

[22] Filed: Nov. 9, 1998

Related U.S. Application Data

[63] Continuation of application No. PCT/EP97/02369, May 9, 1997.

[30] Foreign Application Priority Data

May 10, 1996 [GB] United Kingdom .................. 9609814

[51] Int. Cl.[7] .................................................. G01B 15/02
[52] U.S. Cl. ................................................ 378/54; 378/50
[58] Field of Search ................................. 378/54, 50, 62

[56] References Cited

U.S. PATENT DOCUMENTS

| | | |
|---|---|---|
| 5,138,553 | 8/1992 | Lanza . |
| 5,228,445 | 7/1993 | Pak . |
| 5,594,775 | 1/1997 | Hangartner ............................. 378/207 |
| 5,641,747 | 6/1997 | Popoff et al. ............................ 514/12 |
| 5,748,705 | 5/1998 | Stein et al. ............................... 378/196 |

FOREIGN PATENT DOCUMENTS

| | | |
|---|---|---|
| 411 155 A1 | 2/1991 | European Pat. Off. . |
| 648 467 A1 | 4/1995 | European Pat. Off. . |

*Primary Examiner*—David V. Bruce
*Assistant Examiner*—Michael J. Schwartz
*Attorney, Agent, or Firm*—Pillsbury Madison & Sutro LLP

[57] ABSTRACT

Apparatus for bone densitometry of the wrist is programmed to acquire data from a trapezoidal area (12, 14) of the radius (10) or ulna (11) positioned close to the end plate of the bone avoiding the densely cortical area and extending beyond the turning points bone density measurements on this region of interest show increased responsiveness to biphosphonate and certain other treatment regimes. Other regions of interest may be selected for monitoring still further treatment regimes.

9 Claims, 4 Drawing Sheets

BONE DENSITOMETRY APPARATUS

This is a continuation of International Appln. No. PCT/EP97/02369 filed May 9, 1997 which designated the U.S.

The present invention relates to bone densitometry apparatus in which the data analyzed to produce bone densitometry read outs is taken from a body area selectable according to the treatment regime which a patient is following.

Bones are composed of cortex (compact bone) and trabeculae (connective strands). Regions of bone that experience relatively high stresses tend more toward cortical bone. Regions of bones that experience low stress tend to be more trabecular. In most sites of trabecular bone, the trabecular mass is surrounded by a relatively thin layer of cortical bone which may vary in thickness between individuals.

Osteoporosis is a disease of unknown cause which afflicts people, generally as they age. Osteoporosis affects women more often than men. It is manifest as absolute decrease in bone tissue mass. The bone that remains is, however, normal. A person suffering from osteoporosis loses a greater proportional amount of trabecular bone than cortical bone.

There is a need to be able to take a measurement on a patient and to relate the result reliably both to the results of similar tests on a large number of men and women of different ages so as to gain information on whether the patient is at increased risk of fracture and to previous and future similar measurements on the same patient.

These requirements imply a need to be able to repeat the measurement reliably on the same patient at different times and to make the measurements on many different patients in a consistent way. To this end one defines a region of interest (ROI) in the patient's bones in which measurements will be made, such that the ROI is consistently locatable at each patient measurement event.

The progress of treatment for osteoporosis may be monitored by repeated bone densitometry measurements over time. Such measurements are usually conducted by X-ray bone densitometry in which the attenuation of X-rays by a patient is body or a selected part of it is measured in one of a number of known forms of scanner. Such scanners may make total body measurements or may measure on of a number of particular areas such as a finger bone, the bones of the wrist, the heel bone or one or more vertebrae. Since osteoporosis affects trabecular bone more than cortical bone, the body areas selected are generally those rich in trabecular bone.

It is believed to be the case that treatment with current anti-osteoporosis drug regimes normally results in an increase in bone mass and this is reflected in bone densitometry measurements of the spine or of the hip. Generally no significant increase is seen by bone densitometry of the forearm at the wrist, although a halt is seen in the decline of bone density which is measured if placebo treatment is given.

We have now established that an increase in bone density measurements following treatment can be obtained in measurements on the forearm at the area from which data is taken for processing is sufficiently carefully chosen and that the appropriate area varies according to the treatment regime being followed. More generally, an improved reflection of the effect of treatment can be obtained when an appropriate ROI in any bone under study is selected according to the treatment regime in operation.

Accordingly, in a first aspect, the invention includes apparatus for bone densitometry comprising:

means for acquiring and storing information relating to the density of bone tissue within a body area, means for storing information relating to a plurality of bone disorder treatment regimes, and means for defining a body area in relation to which body area to select information from stored bone density information or from which to acquire said bone density information for processing to derive a bone densitometry read out relating to the defined body area, wherein said defining means is responsive to an operator's choice of a treatment regime out of the treatment regimes for which information is stored.

Preferably, said treatment regimes relate to different medicaments.

Preferably, said information relating to said treatment regimes identifies a respective body area to be defined in said body area defining means in relation to each treatment regime for which information is stored.

Whilst the bone densitometry apparatus is preferably X-ray bone densitometry apparatus, the invention may be applied generally to other forms of densitometer-r apparatus such as ultrasonic bone densitometer.

In a second aspect, the invention includes apparatus for X-ray bone densitometry of the forearm in which bone densitometry read out is obtained from data relating to an area of bone defined in the radius and/or the ulna so as to have a distal boundary lying distal of the turning point between the radius and ulna but proximal of the dense cortical region of the end plate of the bone, and preferably being from 1 to 2 mm proximal from the end plate of the bone, with side edges lying within the bone inside the densely cortical margins of the bone, and extending in the proximal direction beyond the said turning point but without penetrating into regions in which there is more cortical than trabecular bone.

Preferably, the area should be substantially as large as possible within these constraints. Preferably, the length of the area in the distal-proximal direction is approximately the same as the maximum width of the area for the radius and is up to from 1.2 to 1.5 time the maximum width in the ulna. Preferably the area tapers in the proximal direction. The area in the radius preferably has a taper of up to 45° e.g. about 10 to 15° on each side and that in the ulna preferably has a taper of up to 45°, e.g. about 5 to 10° on each side. In each case the area may conveniently be defined as a trapezium.

Preferably said area is defined by locating the turning point between the radius and ulna, constructing a first line from said turning point parallel to the axis of the arm, defining a second line 32 mm proximal from said turning point and at right angles to said first line, defining a point on said second line such that the distance between the intercept of the mid line of the radius and said second line and the intercept of the inner margin of the radius and said second line is equal to the distance from said point to the intercept between the inner margin of the radius and said second line, constructing a reference line from said turning point to said defined point, defining a trapezoid having its longer parallel side on the line between said turning point and the point on the outer edge of the radius or ulna at the same distal proximal level as the turning point such that the distance between said point on the outer edge of the radius or ulna and the adjacent vertex of the trapezoid is equal to the distance between the vertex at the other end of said longer parallel sides and the turning point, moving said trapezoid to a position 1.2 mm proximal of the end plate of the radius or ulna respectively and rotating said trapezoid about the inner vertex involving the longer parallel side thereof until the shorter parallel side thereof is bisected by the mid line of the radius or ulna respectively.

A region of interest as above defined is optimised for monitoring the effect of therapy based on bisphosphonates, such as Alendronate or Ibandronate or for hormone replacement therapy or for fluoride in combination with oestrogens. For other therapies such as calcitonin, or HRT-antagonist treatments, other ROls may advantageously be employed to best reflect the different changes in bone brought about by such therapies. A person skilled in the art may identify suitable ROIs by trial and error in analysing scans from a number of patients undergoing such therapy to find an ROI which shows a response to the treatment appropriately.

Details of such different ROIs may be stored in software or firmware within a scanner according to the invention.

The invention will be further described and illustrated in the following detailed description and in the Examples set out below with reference to the accompanying drawings in which.

Figure 1:
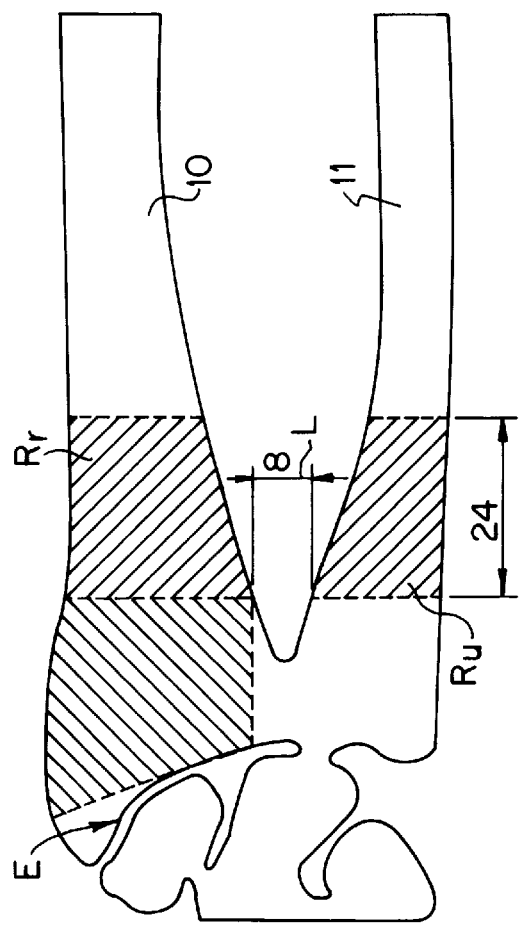
FIG. 1 shows an X-ray bone densitometry image of the distal forearm on which is marked the area from which data is conventionally selected to produce bone densitometry read outs.

FIG. 1 show the bones of the forearm, i.e. the radius 10 and the ulna 11. The region of interest (ROI) used in the past for bone densitometry measurements is shaded at $R_r$ for the radius and at $R_u$ for the ulna. These areas are located with respect to a line L between the radius and the ulna such that L has a length of 8 mm, and extend proximally from the level of the line L. We have now appreciated that the bone in this region does not optimally reflect in bone densitometry the changes which occur in response to bisphosphonate treatment. The bone distal of the line L contains a higher proportion of trabecular bone and we have appreciated that it would be desirable to have an ROI in the area shaded at R. At the same time it is necessary to ensure that one avoids the dense cortical bone of the end plate E of the radius.

Figure 2:
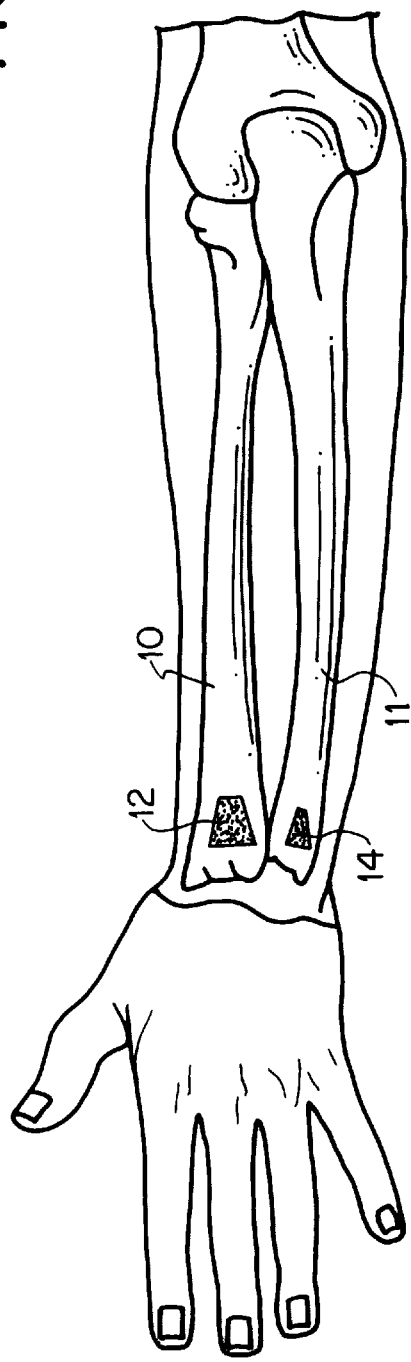
FIG. 2 shows a sketch of the bones of the forearm on which is marked an area appropriate for data selection when monitoring treatment by bisphosphonates.
Figure 3:
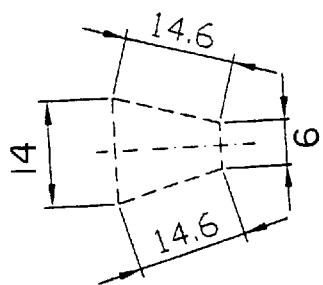
FIG. 3 shows the dimensions of the trapezoidal area 12 in the radius.
Figure 4:
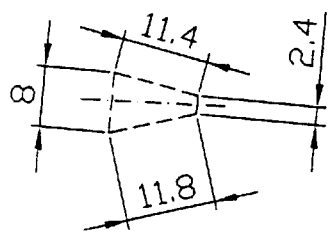
FIG. 4 shows similarly the dimensions of the area 14 in the ulna.
Figure 5:
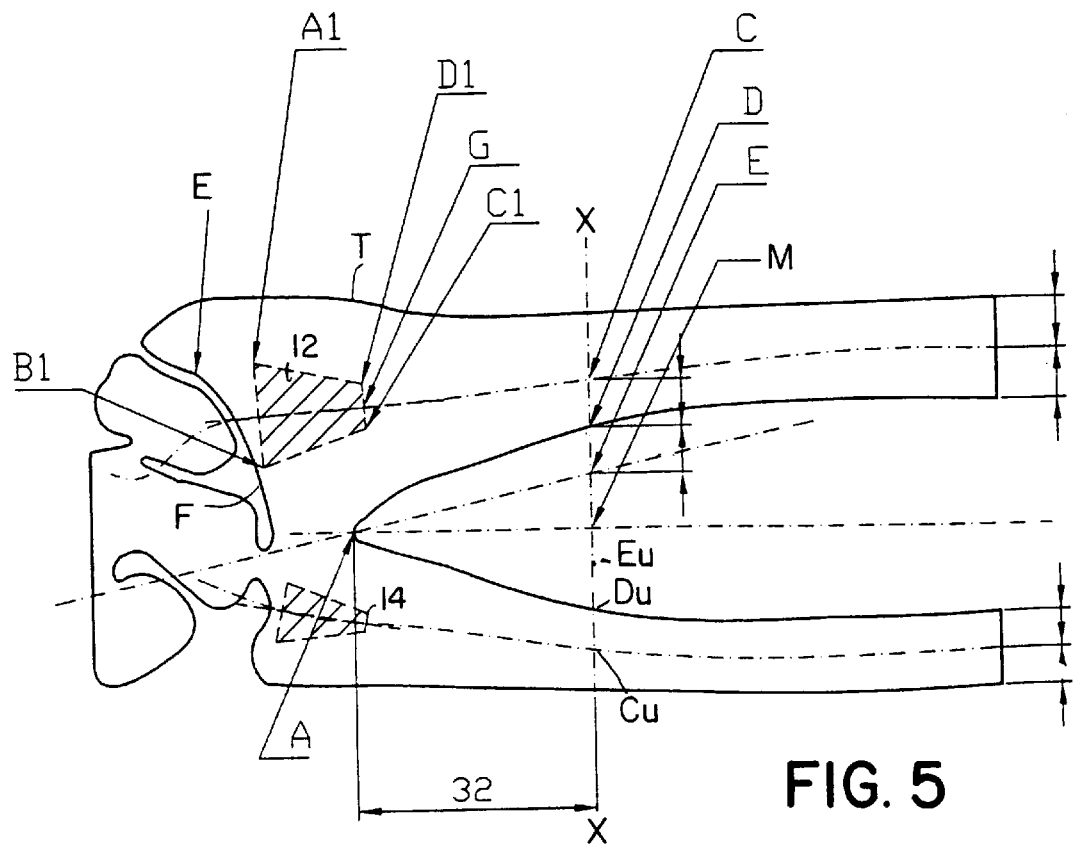
FIG. 5 is an X-ray bone densitometry scan of the distal forearm on which are marked points and lines used in defining the location of the areas 12 and 14.

FIG. 2 shows the bones of the forearm with a region of interest ROI for use according to the invention in monitoring bisphosphonate therapy. The ROI is divided into two spaced sub-areas, the readings from which are summed. Thus toward the distal end of the radius 10 is a first trapezoidal sub-area 12 and toward the distal end of the ulna 14 is a trapezoidal second sub-area 14. The dimensions of these areas are shown in FIGS. 2 and 3. Sub-area 12 has sides of 14 mm, 14.56 mm (2), and 6 mm, whilst sub-area 14 has sides of 8 mm, 11.764 mm (2), and 2.4 mm. The precise dimensions given are default. This total trapezium area, both for radius and ulna can be increased and decreased, in such a way that all 4 lines are moved simultaneously, keeping the shape of the trapezium at all times. The same is the case when decreasing the area. Other dimensions could be chosen within the general constraints described below. The sub-areas are located in a patient's arm in positions deducible by the following procedure. On an X-ray scan of the arm, the junction or turning point between the inside of the radius and the ulna at the position marked A in FIG. 4 is located. A 32 mm line A–M is constructed horizontally in the figure in the proximal direction. A line X—X is constructed through M transverse to A–M 32 mm proximal of A. A point E is constructed on line X—X such that the distance C–D between the intercept of the midline of the radius and the line X—X at C and the intercept between the inner margin of the radius and the line X—X at D is equal to the distance D–E. A reference line A–E is constructed.

Trapezoid 12 of the required dimensions having corners A1, B1, C1 and D1 is positioned such that A1-B1 is on the line A–T, where T is a point defined on the top of the radius, vertically above A in the drawing, i.e., such that the line A–T is at right angles to A–M, and such that T–A1=B1–A. The trapezoid 12 is then moved distally to a position 1.2 mm proximal of the end plate of the radius at F. The trapezoid 12 is then rotated about B1 until the line CI-DI is bisected by the mid line of the radius at G.

The location of the sub-area 12 may now be recorded for is future use as vector coordinates based on the distance of each corner A1, B1, C1 and D1 from the point A, and the angle made with the line A–E by each line joining a respective corner to the point A, eg. the angle between A–Al and the line A–E.

The sub region 14 in the ulna is located by the same procedure, except that the lines and points are reflected across the line A–M, such that the equivalents of C, D and E for example are $C_u$, $D_u$ and $E_u$.

One thereby selects in each case an area which is designed to be as large as possible within the constraints of avoiding the cortical bone at the end plate of the radius or ulna, avoiding the cortical bone at the side edges of the bones, and in the proximal direction avoiding the cortical rich part of the bone that has been measured conventionally in the past. Also, the area as defined above is of course designed to be locatable in different patients in a consistent manner and to be relocatable reliably in the same patient on different occasions.

In practice, bone densitometers scan an area which includes but extends beyond the specific region of interest and present a visual image representing the whole scan. Data is stored for the whole scan. Either automatically or in response to selection by the operator working on the image produced a region of interest is then defined and the bone densitometry read outs are calculated from the data relating to this region only.

In accordance with this invention, the region of interest is defined having regard to the therapeutic treatment to be followed, so reflecting differences in the way in which different therapeutics affect the density of different bone types and areas. The bone densitometry read outs at the start of treatment and at later times as the treatment progresses will all be based on the same region of interest, so that the effect of the treatment may be followed. If later the treatment is changed, new values for the bone densitometry readouts from all the previous scans including the first scan may be calculated appropriate to that new treatment by going back to the stored data for the whole of each previous scan and reselecting a new region of interest, which will also be used in subsequent scans.

The invention will be illustrated by the following examples.

EXAMPLE 1

Figure 6A:
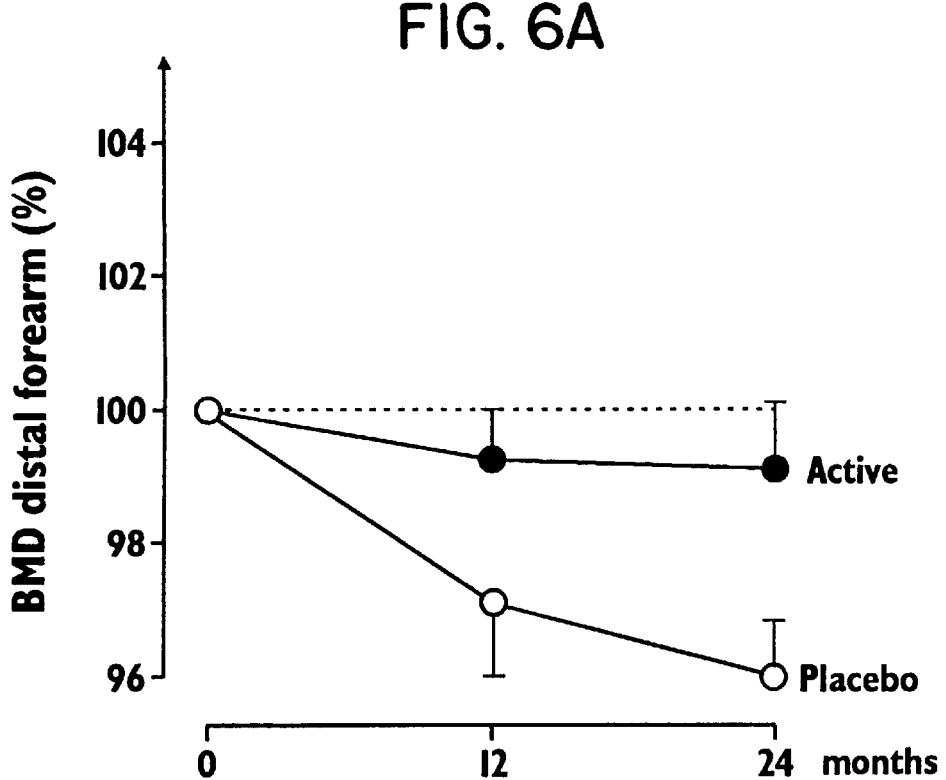
FIG. 6 is a pair of graphs illustrating the results of treatment with Alendronate and Ibandronate respectively as monitored by conventional bone densitometry of the wrist.
Figure 6B:
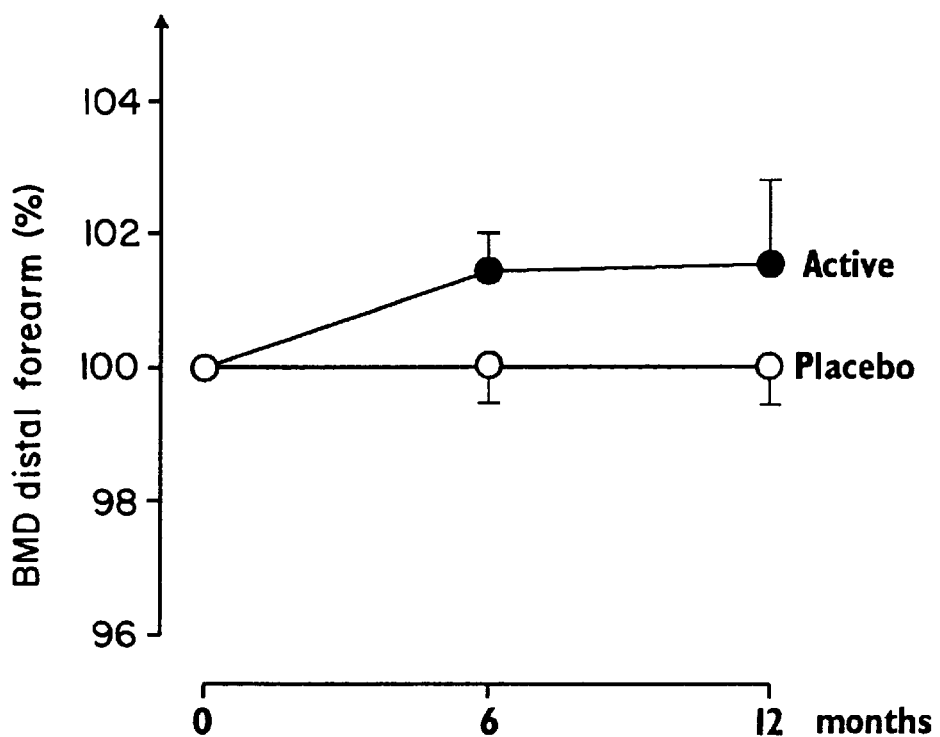

A population of about 20 patients treated with Alendronate (a bisphosphonate) was followed by bone densitometry using a conventional dual energy X-ray forearm scanner over a period of 24 months. The resulting averaged bone mineral density readings based on the areas $R_r$ and $R_u$ of FIG. 1, normalized to a constant starting value and corresponding readings for a patient population of similar size treated with a placebo are shown in Graph A of FIG. 6. A similar set of results is shown in Graph B of FIG. 1 for a similar size group of patients treated for 12 months with the bisphosponate Ibandronate.

It can be seen that whilst a relative improvement compared to the placebo group is shown for the treatment group, no absolute improvement in the patient's condition is demonstrated with Alendronate and with Ibandronate the degree of improvement is small.

The scanner used calculates its bone densitometry readouts from an area of bone illustrated in FIG. 1.

Figure 7A:
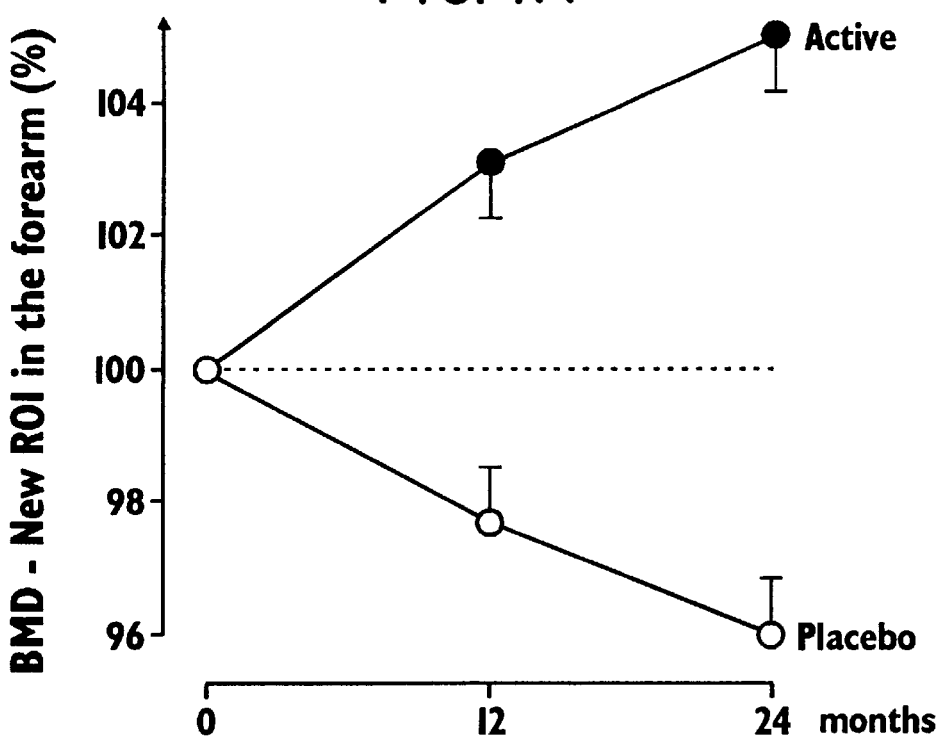
FIG. 7 is a pair of graphs illustrating the results of treatment with Alendronate and Ibandronate respectively as monitored by bone densitometry measurements based on data from the area marked in FIG. 2.
Figure 7B:
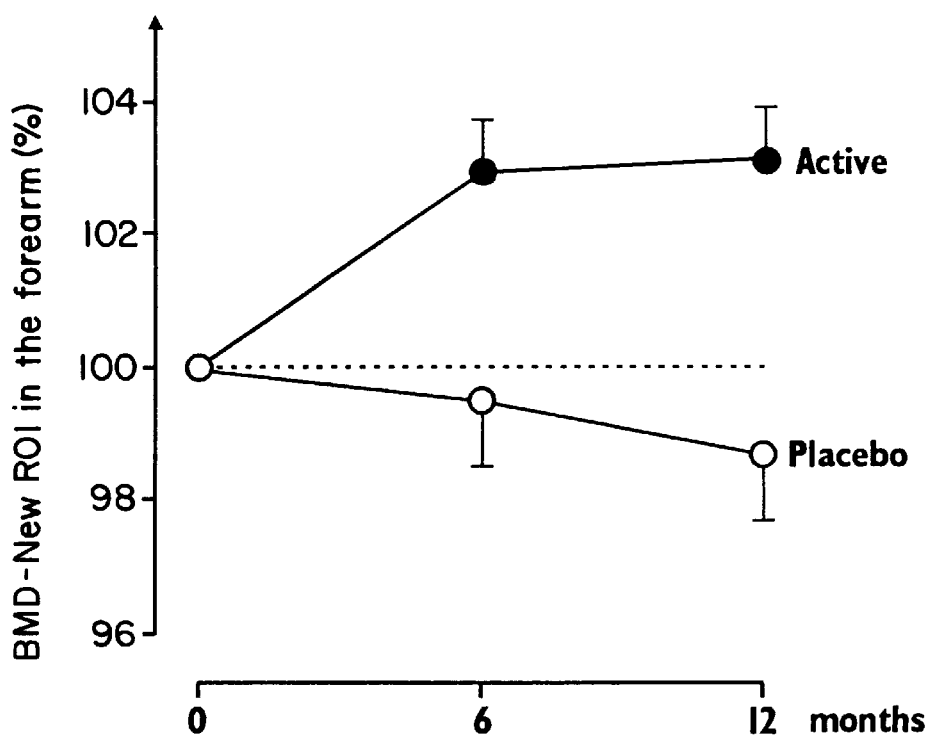

The data for the same patients at the starting time and at each examination during treatment is recalculated selecting readings relating to the area shown in FIG. 2. The results are shown in FIG. 7. It can be seen that an absolute as well as a relative improvement in the patients' condition is now found in Graph A for Alendronate and that a clearer divergence between the treatment and placebo groups is seen in Graph B for Ibandronate.

We claim:

1. Apparatus for bone densitometry comprising
   means for acquiring and storing information relating to a density of bone tissue within a body area,
   means for storing information relating to a plurality of bone disorder treatment regimes, and
   means for defining a body area in relation to which to select information from stored bone density information, or from which to acquire said bone density information, for processing to derive a bone densitometry read out relating to the defined body area,
      wherein said body area defining means is responsive to an operator's choice of a treatment regime out of the treatment regimes for which information is stored.

2. Apparatus as claimed in claim 1, wherein said treatment regimes relate to different medicaments.

3. Apparatus as claimed in claim 1, wherein said information relating to said treatment regimes identifies a respective body area to be defined in said body area defining means in relation to each treatment regime for which information is stored.

4. An apparatus for X-ray bone densitometry of a forearm in which bone densitometry read out is obtained from data relating to an area defined in a radius and/or an ulna so as to have a distal boundary lying distal of a turning point between the radius and the ulna but proximal of a dense cortical region of a end plate of a bone, with side edges lying within the bone inside a densely cortical margins of the bone, and extending in a proximal direction beyond a turning point but without penetrating into regions in which there is more cortical than trabecular bone.

5. Apparatus as claimed in claim 4, wherein said area of bone is of trapezoidal shape having the larger of its two parallel sides positioned distal of the shorter.

6. Apparatus as claimed in claim 4, wherein the length of said area in the distal proximal direction from 0.9 to 1.1 times the maximum width of the area for the radius or is from 1.2 to 1.5 times the maximum width for the ulna.

7. Apparatus as claimed in claim 4, wherein the said area tapers by from 10 to 15° on each side.

8. Apparatus as claimed in claim 5, wherein said trapezoid is defined by locating the turning point between the radius and ulna, constructing a first line from said turning point parallel to the axis of the arm, defining a second line 32 mm proximal from said turning point and at right angles to said first line, defining a point on said second line such that the distance between the intercept of the mid line of the radius and said second line and the intercept of the inner margin of the radius and said second line is equal to the distance from said point to the intercept between the inner margin of the radius and said second line, constructing a reference line from said turning point to said defined point, defining a trapezoid having its longer parallel side on the line between said turning point and the point on the outer edge of the radius or ulna and at the same distal-proximal level as the turning point such that the distance between said point on the outer edge of the radius or ulna and the adjacent vertex of the trapezoid is equal to the distance between the vertex at the other end of said longer parallel sides and the turning point, moving said trapezoid to a position 1.2 mm of the end plate of the radius or ulna respectively and rotating said trapezoid about the inner vertex involving the longer parallel side thereof until the shorter parallel side thereof is bisected by the mid line of the radius or ulna respectively.

9. Apparatus as claimed in claim 4 wherein the size of the trapezoidal region of interest is 14×14.6×6×14.6 mm for the radius or 8×11.4×2.4×11.8 for the ulna.

* * * * *